(12) United States Patent
Cheshire et al.

(10) Patent No.: US 6,900,243 B2
(45) Date of Patent: May 31, 2005

(54) PHENYLHETEROALKYLAMINE DERIVATIVES

(75) Inventors: David Cheshire, Leics (GB); Stephen Connolly, Leics (GB); David Cox, Leics (GB); Antonio Mete, Leics (GB)

(73) Assignee: AstraZeneca AB, Södertalge (SE)

( * ) Notice: Subject to any disclaimer, the term of this patent is extended or adjusted under 35 U.S.C. 154(b) by 54 days.

(21) Appl. No.: 10/204,845

(22) PCT Filed: Feb. 20, 2001

(86) PCT No.: PCT/SE01/00372

§ 371 (c)(1),
(2), (4) Date: Aug. 22, 2002

(87) PCT Pub. No.: WO01/62714

PCT Pub. Date: Aug. 30, 2001

(65) Prior Publication Data

US 2003/0065174 A1 Apr. 3, 2003

(30) Foreign Application Priority Data

Feb. 23, 2000 (GB) .............................................. 0004152

(51) Int. Cl.$^7$ ..................... A61K 31/135; A61K 31/237; C07C 217/18
(52) U.S. Cl. .................... 514/524; 514/649; 514/237.8; 514/239.2; 514/252.12; 514/317; 514/331; 514/408; 514/428; 544/158; 544/165; 544/174; 544/398; 544/402; 546/329; 546/339; 548/569; 548/575; 558/422; 564/341; 564/347; 564/354; 564/367
(58) Field of Search ................................. 564/354, 341, 564/347, 367; 558/422; 514/524, 649

(56) References Cited

U.S. PATENT DOCUMENTS

| | | | |
|---|---|---|---|
| 4,296,126 A | 10/1981 | Nedelec et al. ............. 424/316 |
| 4,314,081 A | 2/1982 | Molloy et al. .............. 564/347 |
| 4,666,910 A | 5/1987 | Schneider et al. .......... 514/228 |
| 4,902,710 A | 2/1990 | Foster et al. ................ 514/438 |
| 6,743,939 B2 * | 6/2004 | Birkinshaw et al. ........ 558/422 |
| 2003/0073685 A1 | 4/2003 | Cheshire et al. .......... 514/227.5 |
| 2003/0139350 A1 | 7/2003 | Larsen et al. ................. 514/25 |
| 2003/0158185 A1 | 8/2003 | Cheshire et al. .......... 514/227.5 |
| 2004/0176422 A1 | 9/2004 | Birkinshaw et al. ........ 514/344 |
| 2004/0242871 A1 | 12/2004 | Birkinshaw et al. ........ 544/183 |

FOREIGN PATENT DOCUMENTS

| | | |
|---|---|---|
| DE | 29 07 217 A1 | 8/1979 |
| EP | 0 273 658 B1 | 7/1988 |
| EP | 0 318 727 A2 | 6/1989 |
| EP | 0 399 504 A2 | 11/1990 |
| EP | 0 515 240 A1 | 11/1992 |
| EP | 0 571 685 A1 | 12/1993 |
| EP | 0 576 766 A1 | 1/1994 |
| EP | 0 661 266 A1 | 7/1995 |
| EP | 0 707 007 A1 | 4/1996 |
| GB | 765849 | 1/1957 |
| GB | 922600 | 4/1963 |
| GB | 1014348 | 12/1965 |
| GB | 2 060 620 A | 5/1981 |
| GB | 2 060 621 A | 5/1981 |
| GB | 2 060 622 A | 5/1981 |
| JP | 51044934 B4 | 12/1976 |
| JP | 52000941 B4 | 1/1977 |
| WO | WO 92/19210 | 11/1992 |
| WO | WO 99/10339 | 3/1999 |
| WO | WO 99/11620 | 3/1999 |
| WO | WO 99/38514 | 8/1999 |
| WO | WO 99/62883 | 12/1999 |
| WO | WO 00/27842 | 5/2000 |
| WO | WO 00/58305 | 10/2000 |
| WO | WO 02/20484 | 3/2002 |
| WO | WO 02/30899 | 4/2002 |

OTHER PUBLICATIONS

S.J. Yan, et al. "Potential causal prophylactic antimalarial agents. Synthesis of quinoxaline, benzimidazole, and alkoxybenzene derivatives containing a novoldiamine moiety." J. Heterocycl. Chem. 297–300, (1978).
Chemical Abstracts, CAPLUS accession No. 1998: 394854 (Zhongguo Yaoke Daxue Xuebao, 1998, 29, 81–91).
Chemical Abstracts, CAPLUS accession No. 1968: 28182 (J. Med. Chem., 1968, 11, 95–97).
Chemical Abstracts, CAPLUS accession No. 1997: 534782 (Zhongguo Yaoke Huaxue Zazhi, 1997, 7, 1–8).
Chemical Abstracts, CAPLUS accession No. 1999: 659361 (WO 99/51575).
Chemical Abstracts, CAPLUS accession No. 1967: 499505 (J. Chem. Soc. B, 1967, 859–866).
Chemical Abstracts, CAPLUS accession No. 1994: 579176 (Tetrahedron Letters, 1994, 35, 4585–4586).
Chemical Abstracts, CAPLUS accession No. 1968: 29366 (Probl. Poluch. Poluprod. Prom. Org. Sin., 1967, 90–97).
Chemical Abstracts, CAPLUS accession No. 1995: 664999 (DE 4 331 179).

(Continued)

*Primary Examiner*—Richard L. Raymond
(74) *Attorney, Agent, or Firm*—Fish & Richardson P.C.

(57) ABSTRACT

There are provided novel compounds of formula (I), wherein $R^1$, $R^2$, X, Y, V, W and Z are as defined in the specification, and pharmaceutically acceptable salts thereof, and enantiomers and racemates thereof; together with processes for their preparation, compositions containing them and their use in therapy. The compounds are inhibitors of nitric oxide synthase and are thereby particularly useful in the treatment or prophylaxis of inflammatory disease and pain.

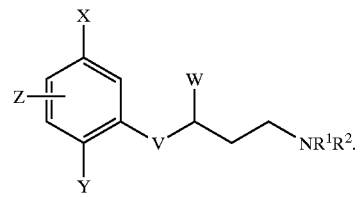

(I)

16 Claims, No Drawings

OTHER PUBLICATIONS

Chemical Abstracts, CAPLUS accession No. 1995: 913361 (WO 95/15954).
Chemical Abstracts, CAPLUS accession No. 1981: 121503 (DE 2 905 877).
Chemical Abstracts, CAPLUS accession No. 1990: 35674 (JP A2 01168666).
Chemical Abstracts, CAPLUS accession No. 1978: 169760 (JP A2 52153922).
Chemical Abstracts, CAPLUS accession No. 1977: 189458 (JP B4 51044934).
Chemical Abstracts, CAPLUS accession No. 1996: 113480 (SU 1824396).
Chemical Abstracts, 1965, vol. 62, 16781 (J. Med. Chem. 1965, 8, 356–367).
Chemical Abstracts, 1958, vol. 52, 11069 (J. Am. Chem. Soc., 1958, 80, 162–164).
Chemical Abstracts, 1966, vol. 65, 2181 (Neth. Appln. 6,508,754).
U.S. Appl. No. 10/483,163, filed Jan. 8, 2004, Cheshire et al.

* cited by examiner

PHENYLHETEROALKYLAMINE DERIVATIVES

CROSS REFERENCE TO RELATED APPLICATIONS

The present application is a national phase application under 35 U.S.C. Section 371 filed from International Patent Application PCT/SE01/00372, filed 20 Feb., 2001 which claims priority to United Kingdom patent application Serial. No. 0004152.5, filed 23 Feb., 2000. The contents of these applications are incorporated herein by reference in their entirety.

FIELD OF THE INVENTION

The present invention relates to novel phenylheteroalkyl amine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been particularly implicated in the pathogenesis of inflammatory diseases. Regulation of these enzymes should therefore offer considerable potential in the treatment of a wide variety of disease states (J. E. Macdonald, *Ann. Rep. Med. Chem.*, 1996, 31, 221–230).

Considerable effort has been expended in efforts to identify compounds that act as specific inhibitors of one or more isoforms of the enzyme nitric oxide synthase. The use of such compounds in therapy has also been widely claimed.

Patent application EP 0 273 658 discloses compounds of formula

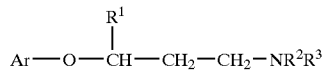

wherein Ar represents phenyl optionally substituted by halogen, C1 to 4 alkyl, C1 to 3 alkoxy or $CF_3$, or optionally substituted naphthyl; $R^1$ represents amongst other things C5 to 7 cycloalkyl; and $R^2$ and $R^3$ are each independently H or methyl. Said compounds are potent and selective inhibitors of serotonin and norepinephrine uptake and are thereby stated to be useful in the treatment of human diseases such as anxiety, depression and obesity.

The present invention relates to the surprising finding that a group of phenylheteroalkylamine derivatives, including some compounds that are within the generic scope of EP 0 273 658, are inhibitors of the enzyme nitric oxide synthase.

DISCLOSURE OF THE INVENTION

According to the present invention, there is provided a compound of formula (I)

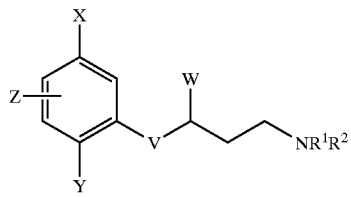

wherein:
X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;
m and p independently represent an integer 0, 1 or 2;
Z represents H or fluoro;
V represents O, $S(O)_n$ or $NR^3$;
W represents C1 to 4 alkyl, C2 to 4 alkenyl, C2 to 4 alkynyl, C3 to 6 cycloalkyl or a 4 to 8 membered saturated heterocyclic ring incorporating one heteroatom selected from O, S and N; any of said groups being optionally further substituted by C1 to 4 alkyl, C1 to 4 alkoxy, C1 to 4 alkylthio, C3 to 6 cycloalkyl, halogen or phenyl; said phenyl group being optionally further substituted by one or more substituents selected independently from halogen, C1 to 4 alkyl, C1 to 4 alkoxy, $CF_3$, $OCF_3$, CN or $NO_2$;
$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
or the group $NR^1R^2$ together represents a 4 to 8 membered saturated azacyclic ring optionally incorporating one further heteroatom selected from O, S or $NR^6$; said ring being optionally substituted by C1 to 4 alkyl, C1 to 4 alkoxy or OH; said alkyl group being optionally substituted by C1 to 4 alkoxy, OH or $NR^7R^8$;
$R^3$ represents H or C1 to 4 alkyl;
$R^4$ and $R^5$ independently represent H or C1 to 4 alkyl;
$R^6$ represents H or C1 to 6 alkyl; said alkyl group being optionally substituted by C1 to 4 alkoxy, OH, $NR^9R^{10}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
$R^7$, $R^8$, $R^9$ and $R^{10}$ independently represent H or C1 to 4 alkyl;
n represents an integer 0, 1 or 2;
or a pharmaceutically acceptable salt, enantiomer or racemate thereof;
with the proviso that when V represents O; and $R^1$ and $R^2$ each independently represent H or methyl; and W represents C5 to 6 cycloalkyl; then at least one of X and Y does not represent halogen, C1 to 4 alkyl, C1 to 3 alkoxy or $CF_3$.

The compounds of formula (I) and their pharmaceutically acceptable salts, enantiomers and racemates have the advantage that they are inhibitors of the enzyme nitric oxide synthase (NOS). In particular, the compounds of formula (I) and their pharmaceutically acceptable salts, enantiomers and racemates have the advantage that they are inhibitors of the inducible isoform of the enzyme nitric oxide synthase (iNOS).

The invention further provides a process for the preparation of compounds of formula (I) or a pharmaceutically acceptable salt, enantiomer or racemate thereof.

According to the invention there is also provided a compound of formula (I), or a pharmaceutically acceptable salt, enantiomer or racemate thereof, for use as a medicament.

Another aspect of the invention provides the use of a compound of formula (I), but without the proviso, or a pharmaceutically acceptable salt, enantiomer or racemate thereof, in the manufacture of a medicament, for the treatment or prophylaxis of diseases or conditions in which inhibition of nitric oxide synthase activity is beneficial.

A more particular aspect of the invention provides the use of a compound of formula (I), but without the proviso, or a pharmaceutically acceptable salt, enantiomer or racemate thereof, in the manufacture of a medicament, for the treatment or prophylaxis of inflammatory disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I), but without the proviso, or a pharmaceutically acceptable salt, enantiomer or racemate thereof.

More particularly, there is also provided a method of treating, or reducing the risk of, inflammatory disease in a person suffering from or at risk of, said disease, wherein the method comprises administering to the person a therapeutically effective amount of a compound of formula (I), but without the proviso, or a pharmaceutically acceptable salt, enantiomer or racemate thereof.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a compound of formula (I), but without the proviso, or a pharmaceutically acceptable salt, enantiomer or racemate thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I), but without the proviso, or a pharmaceutically acceptable salt, enantiomer or racemate thereof in combination with a COX-2 inhibitor.

In one preferred embodiment, V represents O. In another preferred embodiment, V represents S.

In another preferred embodiment, X and Y independently represent Br, Cl, $CH_3$, CN or $CF_3$. It is particularly preferred that X represents Br, Cl or $CF_3$. It is also particularly preferred that Y represents Cl or CN.

Preferably, W represents C1 to 4 alkyl, C2 to 4 alkenyl or C3 to 6 cycloalkyl; optionally substituted by C1 to 4 alkoxy, halogen or phenyl. More preferably, W represents C1 to 4 alkyl.

Preferably, $R^1$ and $R^2$ independently represent H or C1 to 4 alkyl optionally substituted by C1 to 4 alkoxy or hydroxy. More preferably, $R^1$ and $R^2$ independently represent H or methyl.

Particular compounds of the invention include:

3-(2,5-dichlorophenoxy)-N-methyl-1-heptanamine;
3-(2,5-dichlorophenoxy)-N-methyl-1-pentanamine;
[3-cyclopropyl-3-(2,5-dichlorophenoxy)propyl]-N-methyl-1-propanamine;
3-(2,5-dichlorophenoxy)-N,5-dimethyl-1-hexanamine;
3-(2,5-dichlorophenoxy)-N-methyl-1-hexanamine;
4-chloro-2-[3-methyl-1-[2-(methylamino)ethyl]butoxy]benzonitrile;
4-chloro-2-[1-ethyl-3-(methylamino)propoxy]benzonitrile;
4-chloro-2-[1-[2-(methylamino)ethyl]butoxy]benzonitrile;
4-chloro-2-[1-[2-(methylamino)ethyl]pentyloxy]benzonitrile;
4-chloro-2-[1-cyclopropyl-3-(methylamino)propoxy]benzonitrile;
4-chloro-2-[3-(methylamino)-1-(phenylmethyl)propoxy]benzonitrile;
3-(5-chloro-2-nitrophenoxy)-N-methyl-1-heptanamine;
3-(5-chloro-2-nitrophenoxy)-N-methyl-1-pentanamine;
3-[2-chloro-5-(trifluoromethyl)phenoxy]-N-methyl-1-pentanamine;
3-[2-chloro-5-(trifluoromethyl)phenoxy]-N-methyl-1-heptanamine;
3-[(2,5-dichlorophenyl)thio]-N-methyl-1-hexanamine;
4-chloro-2-[1-ethyl-3-(methylamino)propoxy]-5-fluorobenzonitrile;
4-chloro-5-fluoro-2-[1-[2-(methylamino)ethyl]butoxy]benzonitrile;
3-(S-chloro-2-nitrophenoxy)-N-methyl-1-hexanamine;
4-chloro-2-[3-(methylamino)-1-(trifluoromethyl)propoxy]benzonitrile;
4-chloro-5-fluoro-2-[3-(methylamino)-1-(trifluoromethyl)propoxy]benzonitrile;
4-chloro-5-fluoro-[[1-[2-(methylamino)ethyl]-2-propenyl]oxy]benzonitrile;
4-chloro-2-[1-cyclopentyl-3-(methylamino)propoxy]-5-fluorobenzonitrile;
4-chloro-2-{[1-[2-(methylamino)ethyl]butyl]thio)benzonitrile;
4-chloro-2-[1-ethyl-3-[(2-methoxyethyl)amino]propoxy]-5-fluorobenzonitrile;
4-bromo-2-{1-ethyl-3-[(2-methoxyethyl)amino]propoxy}benzonitrile;
4-bromo-2-[3-(dimethylamino)-1-ethylpropoxy]benzonitrile;
4-chloro-2-[3-(dimethylamino)-1-ethylpropoxy]-5-fluorobenzonitrile;
2-[[(1R)-3-amino-1-(methoxymethyl)propyl]oxy]-4-chlorobenzonitrile;

and pharmaceutically acceptable salts, enantiomers or racemates thereof.

Unless otherwise indicated, the term "C1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

The term "C1 to 6 alkyl" is to be interpreted analogously.

Unless otherwise indicated, the term "C3 to 6 cycloalkyl" referred to herein denotes a cycloalkyl group having from 3 to 6 carbon atoms. Examples of such groups include cyclopropyl, cyclopentyl and cyclohexyl.

Unless otherwise indicated, the term "C2 to 4 alkenyl" referred to herein denotes a straight or branched chain alkyl group having from 2 to 4 carbon atoms incorporating at least one carbon-carbon double bond. Examples of such groups include ethenyl, propenyl and butenyl.

Unless otherwise indicated, the term "C2 to 4 alkynyl" referred to herein denotes a straight or branched chain alkyl group having from 2 to 4 carbon atoms incorporating at least one carbon-carbon triple bond. Examples of such groups include ethynyl, propynyl, and butynyl Unless otherwise indicated, the term "C1 to 4 alkoxy" referred to herein denotes a straight or branched chain alkoxy group having from 1 to 4 carbon atoms. Examples of such groups include methoxy, ethoxy, n-propoxy, i-propoxy and t-butoxy.

The term "C1 to 4 alkylthio" is to be interpreted analogously.

Unless otherwise indicated, the term "halogen" referred to herein denotes fluoro, chloro, bromo and iodo.

Examples of a 4 to 8 membered saturated azacyclic ring optionally incorporating one further heteroatom selected from O, S or N include pyrrolidine, piperidine, piperazine, morpholine and perhydroazepine.

Examples of a 4 to 8 membered saturated heterocyclic ring incorporating one heteroatom selected from O, S or N include pyrrolidine, piperidine, tetrahydrofuran and perhydroazepine.

Examples of a five or six membered aromatic heterocyclic ring containing 1 to 3 heteroatoms independently selected from O, S and N include furan, thiophene, pyridine, thiazole, imidazole, oxazole, triazole, oxadiazole, thiadiazole and pyrimidine.

Examples of a five or six membered saturated heterocyclic ring containing 1 to 3 heteroatoms independently selected from O, S and N include pyrrolidine, tetrahydrofuran, piperidine and piperazine.

According to the invention, we further provide a process for the preparation of compounds of formula (I), or a pharmaceutically acceptable salt, enantiomer or racemate thereof which comprises:

(a) reaction of a compound of formula (II)

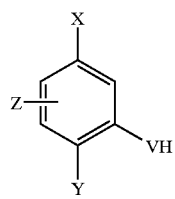

(II)

wherein X, Y, Z and V are as defined in formula (I), with a compound of formula (III)

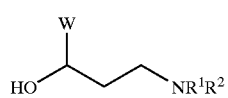

(III)

wherein W, $R^1$ and $R^2$ are as defined in formula (I); or (b) reaction of a compound of formula (IV)

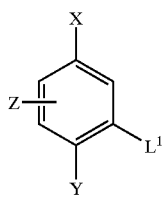

(IV)

wherein X, Y and Z are as defined in formula (I) and $L^1$ represents a leaving group, with a compound of formula (V)

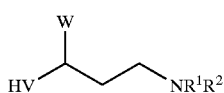

(V)

wherein $R^1$, $R^2$, V and W are as defined in formula (I); or (c) reaction of a compound of formula (VI)

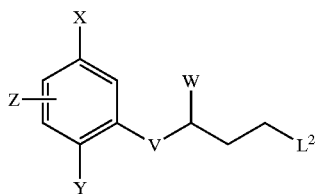

(VI)

wherein X, Y, V, W and Z are as defined in formula (I) and $L^2$ is a leaving group, with a compound of formula (VII)

 HNR$^1$R$^2$ (VII)

wherein $R^1$ and $R^2$ are as defined in formula (I); or (d) reaction of a compound of formula (II)

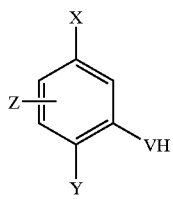

(II)

wherein X, Y, Z and V are as defined in formula (I), with a compound of formula (VIII)

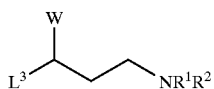

(VIII)

wherein $R^1$, $R^2$ and W are as defined in formula (I) and $L^3$ is a leaving group; or (e) reduction of a compound of formula (IX)

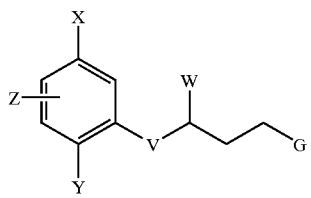

wherein X, Y, V, W and Z are as defined in formula (I) and G represents a group that upon reduction is converted into a group $NR^1R^2$; and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

In process (a), the reactants (II) and (III) are coupled together in a suitable inert solvent such as tetrahydrofuran using, for example, Mitsunobu conditions. Thus, for example, the reactants are treated with a phosphine derivative and an azo derivative at a suitable temperature, generally between 0° C. and the boiling point of the solvent. Suitable phosphine derivatives include triphenylphosphine and tributylphosphine. Suitable azo derivatives include diethyl azodicarboxylate, diisopropyl azodicarboxylate and 1,1'-(azodicarbonyl)dipiperidine.

In process (b), the reaction is performed by treating a nucleophile of formula (V) with an electrophile of formula (IV) in an inert solvent. Suitable leaving groups $L^1$ include halides, particularly fluoride. The reaction is generally performed in the presence of a non-nucleophilic base such as sodium hydride. Suitable organic solvents are those such as N-methyl-2-pyrrolidinone, tetrahydrofuran and dimethylsulfoxide. The reaction is generally conducted at a temperature between 0° C. and the boiling point of the solvent.

Alternatively, in process (b), the reaction will take place using an appropriate palladium source such as palladium (II) acetate in the presence of a suitable phosphine ligand such as BINAP.

In process (c), the amination reaction is performed by reacting a compound of formula (VI) with an amine (VII) in an inert solvent. Suitable leaving groups $L^2$ include sulfonate, trifluorosulfonate, tosylate and halides selected from the group chloride, bromide or iodide. The nucleophile can be a primary or secondary amine in the presence of a base. This base can be either an excess of the amine nucleophile or can be an additive to the reaction mixture. Potential basic additives are metal carbonate, especially alkali metal carbonates, metal oxides and hydroxides, and tertiary amine bases. Suitable organic solvents are those such as acetonitrile, dioxane, N,N-dimethylformamide, N-methyl-2-pyrrolidinone, tetrahydrofuran, dimethylsulfoxide, sulfolane and C1 to 4 alcohols.

In process (d), the reaction is performed by treating a nucleophile of formula (II) with an electrophile of formula (VIII) in an inert solvent. Suitable leaving groups $L^3$ include halides, particularly chloride or bromide. The reaction is generally performed in the presence of a non-nucleophilic base such as sodium hydride. Suitable organic solvents are those such as N-methyl-2-pyrrolidinone, tetrahydrofuran and dimethylsulfoxide. The reaction is generally conducted at a temperature between 0° C. and the boiling point of the solvent.

In process (e), G preferably represents an azido ($N_3$) group. The required reduction may then be achieved by treating a compound of formula (IX) with a suitable reducing agent such as Sn(II) or triphenylphosphine. Preferably the reducing agent is triphenylphosphine and the reduction is carried out in a suitable inert solvent such as tetrahydrofuran.

It will be apparent to a person skilled in the art that in the above processes it may be desirable or necessary to protect an amine, hydroxyl or other potentially reactive group. Suitable protecting groups and details of processes for adding and removing such groups may be found by reference to the standard text "Protecting Groups in Organic Synthesis", 2nd Edition (1991) by Greene and Wuts. In one preferred embodiment, amine groups are protected as carbamate derivatives, for example, as t-butyloxycarbamates. Thus, compounds of formula (I) in which $R^1$ is H are conveniently prepared by removal of a carbamate protecting group from a corresponding compound of formula (I) wherein $R^1$ is a carbamate group, especially a t-butyloxycarbamate group. Removal of the carbamate group is conveniently effected using hydrogen chloride in dioxan.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Certain novel intermediates of formulae (III), (V), (VI), (VIII) and (IX) form another aspect of the invention.

Compounds of formula (III) may be prepared by reaction of a compound of formula (X)

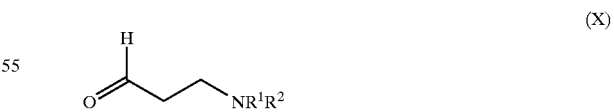

wherein $R^1$ and $R^2$ are as defined in formula (I), with an organometallic derivative, W-M, wherein W is as defined in formula (I) and M represents a metallic residue such as lithium or magnesium-halide, or M represents a silyl residue such as $SiMe_3$.

Compounds of formula (IX) may be prepared by:
(a) reacting a compound of formula (II), as defined above, with a compound of formula (XI)

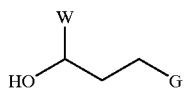

(XI)

wherein W and G are as defined above; or (b) reacting a compound of formula (IV), as defined above, with a compound of formula (XII)

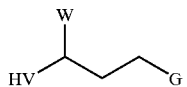

(XII)

wherein V, W and G are as defined above.

Compounds of formulae (II), (IV), (VII), (X), (XI) and (XII) are either known or may be prepared using known methods. Some such methods are illustrated within the Examples that are included herein. Other suitable methods will be readily apparent to the man skilled in the art.

Intermediate compounds may be used as such or in protected form. Protecting groups and details of processes for their removal may be found by reference to the standard text "Protecting Groups in Organic Synthesis", 2nd Edition (1991) by Greene and Wuts.

The compounds of the invention and intermediates thereto may be isolated from their reaction mixtures and, if necessary further purified, by using standard techniques.

The compounds of formula I may exist in enantiomeric forms. Therefore, all enantiomers, diastereomers, racemates and mixtures thereof are included within the scope of the invention.

The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (I), and their pharmaceutically acceptable salts, enantiomers and racemates, are useful because they possess pharmacological activity in animals. In particular, the compounds are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. They may also have utility as inhibitors of the neuronal isoform of the enzyme nitric oxide synthase.

The compounds and their pharmaceutically acceptable salts, enantiomers and racemates are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:
osteoarthritis, rheumatoid arthritis, rheumatoid spondylitis, gouty arhritis and other arthritic conditions, inflamed joints; eczema, psoriasis, dermatitis or other inflammatory skin conditions such as sunburn; inflammatory eye conditions including uveitis, glaucoma and conjunctivitis;
lung disorders in which inflammation is involved, for example, asthma, bronchitis, chronic obstructive pulmonary disease, pigeon fancier's disease, fanner's lung, acute respiratory distress syndrome;
bacteraemia, endotoxaemia (septic shock), aphthous ulcers, gingivitis, pyresis, pain, meningitis and pancreatitis;
conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;
and other conditions associated with inflammation.

The compounds will also be useful in the treatment and alleviation of acute pain or persistent inflammatory pain or neuropathic pain or pain of a central origin.

We are particularly interested in the conditions inflammatory bowel disease, rheumatoid arthritis, osteoarthritis, chronic obstructive pulmonary disease and pain.

The compounds of formula (I) and their pharmaceutically acceptable salts, enantiomers and racemates may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formula (I) may also be useful in the treatment of hypoxia, for example in cases of cardiac arrest and stroke, neurodegenerative disorders including nerve degeneration and/or nerve necrosis in disorders such as ischaemia, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Multiple Sclerosis, Korsakoffs disease, imbecility relating to a cerebral vessel disorder, sleeping disorders, schizophrenia, depression, pain, autism, seasonal affective disorder, jet-lag, depression or other symptoms associated with Premenstrual Syndrome (PMS), anxiety and septic shock. Compounds of formula (I) may also be expected to show activity in the prevention and reversal of drug addiction or tolerance such as tolerance to opiates and diazepines, treatment of drug addiction, treatment of migraine and other vascular headaches, neurogenic inflammation, in the treatment of gastrointestinal motility disorders, cancer and in the induction of labour.

We are particularly interested in the conditions stroke, Alzheimer's disease, Parkinson's disease, multiple sclerosis, schizophrenia, migraine, cancer, septic shock and pain.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt, enantiomer or racemate thereof.

There is also provided a process for the preparation of such a pharmaceutical composition that comprises mixing the ingredients.

The compounds of formula (I), and pharmaceutically acceptable derivatives thereof, may also be advantageously used in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

EXAMPLE 1

3-(2,5-Dichlorophenoxy)-N-methyl-1-heptanamine a) Methyl-(3-oxopropyl)carbamic acid, 1,1-dimethylethyl Ester Dimethylsulfoxide (6.22 ml, 87.6 mmol) was dissolved in dry dichloromethane (100 ml) under nitrogen and the solution was cooled to −78° C. with stirring. Oxalyl chloride (3.95 ml, 45.4 mmol) was then added dropwise and the solution was stirred at −78° C. for a further 30 minutes when effervescence had ceased. A solution of (3-hydroxypropyl) methylcarbamic acid, 1,1-dimethylethyl ester (6.62 g, 35.0 mmol) in dichloromethane (100 ml) was then added dropwise at −78° C. The resultant solution was stirred at −78° C. for 45 minutes, then a solution of triethylamine (24.4 ml, 175 mmol) in dichloromethane (50 ml) was added. The resultant solution was allowed to warm to room temperature and stirred for a further 18 h. The reaction mixture was then poured into brine and extracted with dichloromethane three times. The combined organic fractions were then washed with brine and dried over magnesium sulfate. The solvent was evaporated and the residue triturated with diethyl ether and filtered. The solvent was evaporated to give the title compound (6.60 g, 100%) as an orange oil.

$^1$H NMR 300 MHz (CDCl$_3$) 9.81 (1H, s), 3.55 (2H, t), 2.87 (3H, s), 2.68 (2H, t), 1.45 (9H, s).

b) (3-Hydroxyheptyl)methylcarbamic acid, 1,1-dimethylethyl ester

Methyl-(3-oxopropyl)carbamic acid, 1,1-dimethylethyl ester (2.00 g, 10.7 mmol) was dissolved in tetrahydrofuran (20 ml) under nitrogen and cooled to 0° C. with stirring. To the resulting solution was added n-butylmagnesium chloride and the mixture stirred at 0° C. for a further 30 minutes and then allowed to warm to room temperature with stirring over 20 h. The mixture was then poured into saturated ammonium chloride solution and then extracted with diethyl ether three times. The combined organic fractions were then washed with brine and dried over magnesium sulfate. The solvent was evaporated and the residue eluted down a flash chromatography column using 40% diethyl ether/isohexane as eluent to give 1.70 g (65%) of the title compound as an oil.

$^1$H NMR 300 MHz (CDCl$_3$) 3.70 (1H, bs), 3.47 (1H, bs), 3.03 (1H, bs), 2.83 (3H, s), 1.68 (1H, m), 1.17–1.53 (17H, m), 0.90 (3H, t).

c) [3-(2,5-Dichlorophenoxy)heptyl]methylcarbamic acid, 1-dimethylethyl ester 2,5-Dichlorophenol (163 mg, 1.00 mmol) and (3-hydroxyheptyl)methylcarbamic acid, 1,1-dimethylethyl ester (360 mg, 1.47 mmol) were dissolved in tetrahydrofuran (10 ml). To the resulting solution was added tributylphosphine (0.380 ml, 1.50 mmol) and then 1,1'-(azodicarbonyl)dipiperidine (380 mg, 1.50 mmol). The solution was then heated to 50° C. under nitrogen for 3 h, and then allowed to stir at room temperature for a further 20 h. The mixture was then filtered and poured into sodium hydrogen carbonate solution. The mixture was extracted with diethyl ether three times and the combined organic fractions were washed with brine, then dried over magnesium sulfate. The solvent was evaporated and the residue eluted down a flash chromatography column using 10% ethyl acetate/isohexane as eluent to give 200 mg (51%) of the title compound as an oil.

$^1$H NMR 300 MHz (CDCl$_3$) 7.23–7.29 (1H, m), 6.85–6.91 (2H, m), 4.29 (1H, t), 3.35 (2H, t), 2.84 (3H, s), 1.86–1.95 (2H, m), 1.70 (2H, bm), 1.35–1.45 (13H, m), 0.89 (3H, t).

d) 3-(2,5-Dichlorophenoxy)-N-methyl-1-heptanamine fumarate

[3-(2,5-Dichlorophenoxy)heptyl]methylcarbamic acid, 1,1-dimethylethyl ester (190 mg, 0.487 mmol) was dissolved in 4M hydrogen chloride in dioxane (6 ml). The resulting solution was stirred at room temperature for 2 h, then the solvent was evaporated. The residue was diluted with dichloromethane and washed with sodium bicarbonate solution containing ammonia, then dried over magnesium sulfate. The solvent was evaporated and the residue dissolved in ethanol. To this solution was added fumaric acid in ethanol and the solvent evaporated. The residue was recrystallised from diethyl ether/ethanol to give 75 mg (38%) of the title compound as a white solid.

MS APCI+ve$^m$/z 290 ([M+H]$^+$). $^1$H NMR 300 MHz (d$_6$-DMSO) 7.45 (1H, d), 7.34 (1H, d), 7.01 (1H, dd), 6.44 (2H, s), 4.65 (1H, m), 2.81–2.94 (2H, m), 2.45 (3H, s), 1.93 (2H, q), 1.59 (2H, m), 1.24–1.35 (4H, m), 0.85 (3H, t).

EXAMPLE 2

3-(2,5-Dichlorophenoxy)-N-methyl-1-pentanamine a) (3-Hydroxypentyl)methylcarbamic acid, 1,1-dimethylethyl ester The title compound was prepared according to the method of Example 1 step (b) but using ethylmagnesium bromide.

$^1$H NMR 300 MHz (CDCl$_3$) 3.90 (1H, m), 2.90–3.50 (2H, m), 2.85 (3H, s), 1.70 (2H, m), 1.50 (11H, m), 0.96 (3H, t).

b) [3-(2,5-Dichlorophenoxy)pentyl]methylcarbamic acid 1,1-dimethylethyl ester 2,5-Dichlorophenol (325 mg, 2.00 mmol) and (3-hydroxypentyl)methylcarbamic acid, 1,1-dimethylethyl ester (217 mg, 1.00 mmol) were dissolved in tetrahydrofuran (10 ml). To the resulting solution was added triphenylphosphine (393 mg, 1.50 mmol) and then diethyl azodicarboxylate (0.240 ml, 1.52 mmol). The solution was then allowed to stir at room temperature under nitrogen for 24 h. The mixture was then poured into water and extracted three times with diethyl ether. The combined organic fractions were washed with 1N sodium hydroxide solution twice and then brine and dried over magnesium sulfate. The solvent was evaporated and the residue eluted down a flash chromatography column using 10% ethyl acetate/isohexane as eluent to give 180 mg (50%) of the title compound as an oil.

$^1$H NMR 300 MHz (CDCl$_3$) 7.26 (1H, m), 6.84 (2H, m), 4.24 (1H, m), 3.36 (2H, t), 2.84 (3H, s), 1.92 (2H, m), 1.74 (2H, m), 1.43 (9H, s), 0.98 (3H, t).

c) 3-(2,5-Dichlorophenoxy)-N-methyl-1-pentanamine hydrochloride

[3-(2,5-Dichlorophenoxy)pentyl]methylcarbamic acid, 1,1-dimethylethyl ester (180 mg, 0.487 mmol) was dissolved in 4M hydrogen chloride in dioxane (6 ml). The resulting solution was stirred at room temperature for 3 h, then the solvent was evaporated. The residue was recrystallised from diethyl ether/ethanol to give 130 mg (88%) of the title compound as a white solid.

MS APCI+ve $^m$/z 262/4 ([M+H]$^+$). $^1$H NMR 300 MHz (d$_6$-DMSO) 8.75 (1H, bs), 7.47 (1H, d), 7.35 (1H, d), 7.04 (1H, dd), 4.65 (1H, m), 2.90–3.04 (2H, m), 2.55 (3H, s), 1.99 (2H, q), 1.64 (2H, m), 0.90 (3H, t).

EXAMPLE 3

[3-Cyclopropyl-3-(2,5-dichlorophenoxy)]-N-methyl-1-propanamine fumarate a) (3-Cyclopropyl-3-hydroxypropyl)methylcarbamic Acid, 1,1-dimethylethyl ester The title compound was prepared according to the method of Example 1 step (b) but using cyclopropylmagnesium bromide.

$^1$H NMR 300 MHz (CDCl$_3$) 3.00–3.85 (3H, m), 2.80 (4H, m), 1.82 (1H, m), 1.45 (11H, m), 0.90 (1H, m), 0.53 (m, 1H), 0.31 (2H, m), 0.18 (1H, m).

b) [3-Cyclopropyl-3-(2,5-dichlorophenoxy)propyl]methylcarbamic Acid, 1,1-dimethylethyl ester 1,4-Dichloro-2-fluorobenzene (165 mg, 1.00 mmol) and (3-cyclopropyl-3-hydroxypropyl)methylcarbamic acid, 1,1-dimethylethyl ester (230 mg, 1.00 mmol) were dissolved in dimethylsulfoxide (10 ml) under nitrogen at room temperature. To the resulting solution was added sodium hydride (60% in oil) (80 mg, 2.00 mmol). The solution was then allowed to stir at room temperature under nitrogen for 24 h. The mixture was then poured into water and extracted with diethyl ether three times. The combined organic fractions were washed with brine and dried over magnesium sulfate. The solvent was evaporated and the residue eluted down a flash chromatography column using 10% ethyl acetate/isohexane as eluent to give 175 mg (47%) of the title compound as an oil.

$^1$H NMR 300 MHz (CDCl$_3$) 7.26 (1H, m), 6.96 (1H, s), 6.87 (1H, m), 3.80 (1H, q), 3.42 (2H, m), 2.84 (3H, s), 2.01 (2H, m), 1.43 (9H, s), 1.10 (1H, m), 0.54 (2H, d), 0.30 (2H, bm).

c) [3-Cyclopropyl-3-(2,5-dichlorophenoxy)]-N-methyl-1-propanamine fumarate

The title compound was prepared according to the method of Example 1 step (d) but using [3-cyclopropyl-3-(2,5-dichlorophenoxy)propyl]methylcarbamic acid, 1,1-dimethylethyl ester.

MS APCI+ve $^m$/z 274/6 ([M+H]$^+$). $^1$H NMR 300 MHz (d$_6$-DMSO) 7.45 (1H, d), 7.36 (1H, d), 7.03 (1H, dd), 6.44 (2H, s), 4.13 (1H, q), 2.91 (2H, m), 2.50 (3H, s), 2.01 (2H, q), 1.08 (1H, m), 0.49 (2H, m), 0.26 (2H, m).

EXAMPLE 4

3-(2,5-Dichlorophenoxy)-N,5-dimethyl-1-hexanamine fumarate a) (3-Hydroxy-5-methylhexyl)methylcarbamic acid, 1,1-dimethylethyl ester The title compound was prepared according to the method of Example 1 step (b) but using 2-methylpropylmagnesium bromide.

$^1$H NMR 300 MHz (CDCl$_3$) 3.95 (1H, m), 3.45 (2H, bm), 2.85 (4H, bm), 1.80 (2H, bm), 1.64 (2H, bm), 1.47 (10H, m), 0.91 (6H, m).

b) [3-(2,5-Dichlorophenoxy)-5-methylhexyl]methylcarbamic Acid, 1,1-dimethylethyl ester The title compound was prepared according to the method of Example 1 step (c) but using (3-hydroxy-5-methylhexyl) methylcarbamic acid, 1,1-dimethylethyl ester.

MS APCI+ve $^m$/z 290/2/4 ([M+H-Boc]$^+$).

c) 3-(2,5-Dichlorophenoxy)-N,5-dimethyl-1-hexanamine fumarate

The title compound was prepared according to the method of Example 1 step (d) but using [3-(2,5-dichlorophenoxy)-5-methylhexyl]methylcarbamic acid, 1,1-dimethylethyl ester.

MS APCI+ve $^m$/z 290 ([M+H]$^+$). $^1$H NMR 300 MHz (d$_6$-DMSO) 7.45 (1H, d), 7.38 (1H, d), 7.01 (1H, dd), 6.44 (2H, s), 4.72 (1H, m), 2.85 (2H, m), 2.50 (3H, s), 1.94 (2H, m), 1.53–1.73 (2H, m), 1.43 (1H, m), 0.89 (6H, dd).

EXAMPLE 5

3-(2,5-Dichlorophenoxy)-N-methyl-1-hexanamine hydrochloride a) (3-Hydroxyhexyl)methylcarbamic Acid, 1,1-dimethylethyl ester The title compound was prepared according to the method of Example 1 step (b) but using propylmagnesium chloride.

$^1$H NMR 300 MHz (CDCl$_3$) 3.90 (1H, in), 2.90–3.50 (2H, bm), 2.84 (3H, s), 1.65 (2H, m), 1.50 (13H, m), 0.90 (3H, t).

b) [3-(2,5-Dichlorophenoxy)hexyl]methylcarbamic Acid 1,1-dimethylethyl ester

The title compound was prepared according to the method of Example 3 step (b) but using 2,5-dichlorofluorobenzene and (3-hydroxyhexyl)methylcarbamic acid, 1,1-dimethylethyl ester.

$^1$H NMR 300 MHz (CDCl$_3$) 7.26 (1H, m), 6.86 (2H, m), 4.29 (1H, m), 3.33 (2H, m), 2.83 (3H, s), 1.92 (2H, m), 1.68 (2H, m), 1.45 (11H, m), 0.95 (3H, t).

c) 3-(2,5-Dichlorophenoxy)-N-methyl-1-hexanamine hydrochloride

The title compound was prepared according to the method of Example 2 step (c) but using [3-(2,5-dichlorophenoxy) hexyl]methylcarbamic acid, 1,1-dimethylethyl ester.

MS APCI+ve $^m$/z 276 ([M+H]$^+$). $^1$H NMR 300 MHz (d$_6$-DMSO) 8.77 (2H, bs), 7.47 (1H, d), 7.37 (1H, d), 7.04 (1H, dd), 4.70 (1H, m), 2.99 (2H, m), 2.54 (3H, s), 2.00 (2H, m), 1.60 (2H, m), 1.33 (2H, m), 0.89 (3H, t).

EXAMPLE 6

4-Chloro-2-[3-methyl-1-[2-(methylamino)ethyl]butoxy]benzonitrile fumarate a) [3-(5-Chloro-2-cyanophenoxy)-5-methylhexyl]methylcarbamic Acid 1,1-dimethylethyl ester The title compound was prepared according to the method of Example 2 step (b) but using 4-chloro-2-hydroxybenzonitrile and (3-hydroxy-5-methylhexyl)methylcarbamic acid, 1,1-dimethylethyl ester.

MS APCI+ve $^m/z$ 281 ([M+H-Boc]$^+$).

b) 4-Chloro-2-[3-methyl-1-[2-(methylamino)ethyl]butoxy]benzonitrile fumarate

The title compound was prepared according to the method of Example 1 step (d) but using 3-(5-chloro-2-cyanophenoxy)-5-methylhexyl]methylcarbamic acid, 1,1-dimethylethyl ester.

MS APCI+ve $^m/z$ 281/3 ([M+H]$^+$). $^1$H NMR 300 MHz (d$_6$-DMSO) 7.77 (1H, d), 7.53 (1H, s), 7.17 (1H, d), 6.44 (2H, s), 4.81 (1H, m), 2.68 (2H, m), 2.47 (3H, s), 1.95 (2H, m), 1.57–1.73 (2H, m), 1.45 (1H, m), 0.89 (6H, dd).

EXAMPLE 7

4-Chloro-2-[1-ethyl-3-(methylamino)propoxy]benzonitrile hydrochloride a) [3-(5-Chloro-2-cyanophenoxy)pentyl]methylcarbamic Acid, 1,1-dimethylethyl ester The title compound was prepared according to the method of Example 3 step (b) but using (3-hydroxypentyl)methylcarbamic acid, 1,1-dimethylethyl ester and 4-chloro-2-fluorobenzonitrile.

MS APCI+ve $^m/z$ 252/4 ([M+H-Boc]$^+$).

b) 4-Chloro-2-[1-ethyl-3-(methylamino)propoxy]benzonitrile hydrochloride

The title compound was prepared according to the method of Example 2 step (c) but using [3-(5-chloro-2-cyanophenoxy)pentyl]methylcarbamic acid, 1,1-dimethylethyl ester.

MS APCI+ve $^m/z$ 253/5 ([M+H]$^+$). $^1$H NMR 300 MHz (d$_6$-DMSO) 8.85 (2H, bs), 7.79 (1H, d), 7.52 (1H, d), 7.19 (1H, dd), 4.79 (1H, m), 2.98 (2H, m), 2.55 (3H, s), 2.02 (2H, q), 1.67 (2H, m), 0.91 (3H, t).

EXAMPLE 8

4-Chloro-2-[1-[2-(methylamino)ethyl]butoxy]benzonitrile hydrochloride a) [3-(5-Chloro-2-cyanophenoxy)hexyl]methylcarbamic Acid 1,1-dimethylethyl ester The title compound was prepared according to the method of Example 3 step (b) but using 4-chloro-2-fluorobenzonitrile and (3-hydroxyhexyl)methylcarbamic acid 1,1-dimethylethyl ester.

MS APCI+ve $^m/z$ 267/9 ([M+H-Boc]$^+$).

b) 4-Chloro-2-[1-[2-(methylamino)ethyl]butoxy]benzonitrile hydrochloride

The title compound was prepared according to the method of Example 2 step (c) but using [3-(5-chloro-2-cyanophenoxy)hexyl]methylcarbamic acid, 1,1-dimethylethyl ester.

MS APCI+ve $^m/z$ 267/9 ([M+H]$^+$). $^1$H NMR 300 MHz (d$_6$-DMSO) 8.82 (2H, bs), 7.79 (1H, d), 7.52 (1H, d), 7.19 (1H, dd), 4.84 (1H, m), 2.99 (2H, m), 2.54 (3H, s), 2.02 (2H, m), 1.63 (2H, m), 1.35 (2H, m), 0.90 (3H, t).

EXAMPLE 9

4-Chloro-2-[1-[2-(methylamino)ethyl]pentyloxy]benzonitrile fumarate a) [3-(5-Chloro-2-cyanophenoxy)heptyl]methylcarbamic acid 1,1-dimethylethyl ester 2,4-Dichlorobenzonitrile (206 mg, 1.20 mmol), potassium benzoate (160 mg, 1.00 mmol) and (3-hydroxyheptyl)methylcarbanic acid, 1,1-dimethylethyl ester (245 mg, 1.00 mmol) were dissolved in dimethylsulfoxide (3 ml) under nitrogen at room temperature. To the resulting solution was added sodium hydride (60% in oil) (45 mg, 1.10 mmol). The solution was then allowed to stir at room temperature under nitrogen for 24 h. The mixture was then poured into water and extracted with diethyl ether three times. The combined organic fractions were washed with brine and dried over magnesium sulfate. The solvent was evaporated and the residue eluted down a flash chromatography column using 10% diethyl ether/isohexane as eluent to give 110 mg (29%) of the title compound as an oil.

$^1$H NMR 300 MHz (CDCl$_3$) 7.47 (1H, d), 6.97 (1H, d), 6.92 (1H, bs), 4.37 (1H, m), 3.38 (2H, m), 2.85 (3H, s), 1.96 (2H, m), 1.72 (2H, m), 1.33–1.45 (13H, m), 0.91 (3H, t).

b) 4-Chloro-2-[1-[2-(methylamino)ethyl]pentyloxy]benzonitrile fumarate

The title compound was prepared according to the method of Example 1 step (d) but using [3-(5-chloro-2-cyanophenoxy)heptyl]methylcarbamic acid, 1,1-dimethylethyl ester.

MS APCI+ve $^m/z$ 281/3 ([M+H]$^+$). $^1$H NMR 300 MHz (d$_6$-DMSO) 7.77 (1H, d), 7.50 (1H, d), 7.16 (1H, dd), 6.44 (2H, s), 4.77 (1H, m), 2.84 (2H, m), 2.47 (3H, s), 1.94 (2H, m), 1.62 (2H, m), 1.27–1.35 (4H, m), 0.85 (3H, t).

EXAMPLE 10

4-Chloro-2-[1-cyclopropyl-3-(methylamino)propoxy]benzonitrile hydrochloride a) [3-(5-Chloro-2-cyanophenoxy)-3-cyclopropylpropyl]methylcarbamic acid, 1,1-dimethylethyl ester The title compound was prepared according to the method of Example 3 step (b) but using 4-chloro-2-fluorobenzonitrile and (3-cyclopropyl-3-hydroxypropyl)methylcarbamic acid, 1,1-dimethylethyl ester.

MS APCI+ve $^m/z$ 265/7 ([M+H-Boc]$^+$).

b) 4-Chloro-2-[1-cyclopropyl-3-(methylamino)propoxy]benzonitrile hydrochloride

The title compound was prepared according to the method of Example 2 step (c) but using [3-(5-chloro-2-cyanophenoxy)-3-cyclopropylpropyl]methylcarbamic acid, 1,1-dimethylethyl ester.

MS APCI+ve $^m/z$ 265/7 ([M+H]$^+$). $^1$H NMR 300 MHz (d$_6$-DMSO) 8.77 (2H, bs), 7.79 (1H, d), 7.53 (1H, d), 7.20 (1H, dd), 4.33 (1H, q), 3.06 (2H, m), 2.56 (3H, s), 2.09 (2H, q), 1.12 (1H, m), 0.53 (2H, m), 0.32 (2H, m).

EXAMPLE 11

4-Chloro-2-[3-(methylamino)-1-(phenylmethyl)propoxy]benzonitrile fumarate a) (3-Hydroxy-4-phenylbutyl)methylcarbamic Acid 1,1-dimethylethyl ester The title compound was prepared according to the method of Example 1 step (b) but using benzylmagnesium chloride.

¹H NMR 300 MHz (CDCl₃) 7.21–7.32 (5H, m), 3.80 (2H, m), 2.80 (4H, m), 1.70 (1H, m), 1.44–1.48 (12H, m).

b) [3-(5-Chloro-2-cyanophenoxy)-4-phenylbutyl] methylcarbamic acid, 1,1-dimethylethyl ester The title compound was prepared according to the method of Example 3 step (b) but using (3-hydroxy-4-phenylbutyl) methylcarbamic acid, 1,1-dimethylethyl ester, and 4-chloro-2-fluorobenzonitrile.

¹H NMR 300 MHz (CDCl₃) 7.44 (1H, m), 7.26 (5H, m), 6.91 (1H, m), 6.79 (1H, m), 4.55 (1H, m), 3.38 (2H, m), 3.03 (2H, m), 2.79 (3H, s), 1.95 (2H, m), 1.37 (9H, s).

c) 4-Chloro-2-[3-(methylamino)-1-(phenylmethyl) propoxy]benzonitrile fumarate

The title compound was prepared according to the method of Example 1 step (d) but using [3-(5-chloro-2-cyanophenoxy)-4-phenylbutyl]methylcarbamic acid, 1,1-dimethylethyl ester.

MS APCI+ve $^m/z$ 315/7 ([M+H]⁺). ¹H NMR 300 MHz (d₆-DMSO) 7.72 (1H, d), 7.39 (1H, d), 7.16–7.28 (5H, m), 7.11 (1H, dd), 6.44 (2H, s), 5.03 (1H, m), 2.84–3.03 (4H, m), 2.45 (3H, s), 1.95 (2H, m).

EXAMPLE 12

3-(5-Chloro-2-nitrophenoxy)-N-methyl-1-heptanamine fumarate a) [3-(5-Chloro-2-nitrophenoxy)heptyl]methylcarbamic acid, 1,1-dimethylethyl ester The title compound was prepared according to the method of Example 3 step (b) but using (3-hydroxyheptyl) methylcarbamic acid, 1,1-dimethylethyl ester and 4-chloro-2-fluoronitrobenzene.

¹H NMR 300 MHz (CDCl₃) 7.77 (1H, d), 6.98 (2H, m), 4.41 (1H, m), 3.36 (2H, t), 2.83 (3H, s), 1.93 (2H, m), 1.72 (2H, m), 1.28–1.41 (13H, m), 0.90 (3H, t).

b) 3-(5-Chloro-2-nitrophenoxy)-N-methyl-1-heptanamine Fumarate

The title compound was prepared according to the method of Example 1 step (d) but using [3-(5-chloro-2-nitrophenoxy)heptyl]methylcarbamic acid, 1,1-dimethylethyl ester.

MS APCI+ve $^m/z$ 301 ([M+H]⁺). ¹H NMR 300 MHz (d₆-DMSO) 7.90 (1H, d), 7.58 (1H, d), 7.18 (1H, dd), 6.47 (2H, s), 4.82 (1H, m), 2.90 (2H, m), 2.50 (3H, s), 1.94 (2H, m), 1.60 (2H, m), 1.30 (4H, m), 0.85 (3H, t).

EXAMPLE 13

3-(5-Chloro-2-nitrophenoxy)-N-methyl-1-pentanamine hydrochloride a) [3-(5-Chloro-2-nitrophenoxy)pentyl]methylcarbamic Acid, 1,1-dimethylethyl ester The title compound was prepared according to the method of Example 3 step (b) but using (3-hydroxypentyl) methylcarbamic acid, 1,1-dimethylethyl ester and 4-chloro-2-fluoronitrobenzene.

¹H NMR 300 MHz (CDCl₃) 7.78 (1H, d), 7.02 (1H, s), 6.97 (1H, d), 4.38 (1H, m), 3.37 (2H, t), 2.84 (3H, s), 1.96 (2H, m), 1.77 (2H, m), 1.41 (9H, s), 0.99 (3H, t).

b) 3-(5-Chloro-2-nitrophenoxy)-N-methyl-1-pentanamine hydrochloride

The title compound was prepared according to the method of Example 2 step (c) but using [3-(5-chloro-2-nitrophenoxy)pentyl]methylcarbamic acid, 1,1-dimethylethyl ester.

MS APCI+ve $^m/z$ 273/5 ([M+H]⁺). ¹H NMR 300 MHz (d₆-DMSO) 8.67 (2H, bs), 7.92 (1H, d), 7.59 (1H, d), 7.20 (1H, dd), 4.82 (1H, m), 3.32 (3H, s), 2.97 (2H, m), 2.55 (3H, s), 1.99 (2H, m), 1.66 (2H, m), 0.89 (3H, t).

EXAMPLE 14

3-[2-Chloro-5-(trifluoromethyl)phenoxy]-N-methyl-1-pentanamine hydrochloride a) [3-[2-Chloro-5-(trifluoromethyl)phenoxy]pentyl] methylcarbamic Acid, 1,1-dimethylethyl ester The title compound was prepared according to the method of Example 2 step (b) but using (3-hydroxypentyl) methylcarbamic acid, 1,1-dimethylethyl ester and 2-chloro-5-(trifluoromethyl)phenol.

¹H NMR 300 MHz (CDCl₃) 7.46 (1H, d), 7.13 (1H, d), 7.09 (1H, s), 4.32 (1H, m), 3.36 (2H, m), 2.84 (3H, s), 1.96 (2H, m), 1.76 (2H, t), 1.40 (9H, s), 0.99 (3H, t).

b) 3-[2-Chloro-5-(trifluoromethyl)phenoxy]-N-methyl-1-pentanamine hydrochloride

The title compound was prepared according to the method of Example 2 step (c) but using [[3-[2-chloro-5-(trifluoromethyl)phenoxy]pentyl]methylcarbamic acid, 1,1-dimethylethyl ester.

MS APCI+ve $^m/z$ 296/8 ([M+H]⁺). ¹H NMR 300 MHz (d₆-DMSO) 8.72 (2H, bs), 7.70 (1H, d), 7.53 (1H, s), 7.34 (1H, d), 4.78 (1H, m), 3.32 (3H, s), 2.98 (2H, m), 2.55 (3H, s), 2.01 (2H, q), 1.65 (2H, m), 0.90 (3H, t).

EXAMPLE 15

3-[2-Chloro-5-(trifluoromethyl)phenoxy]-N-methyl-1-heptanamine hydrochloride a) [3-[2-Chloro-5-(trifluoromethyl)phenoxy]heptyl] methylcarbamic acid, 1,1-dimethylethyl ester The title compound was prepared according to the method of Example 1 step (c) but using 2-chloro-5-(trifluoromethyl) phenol and (3-hydroxyheptyl)methylcarbamic acid, 1,1-dimethylethyl ester.

¹H NMR 300 MHz (CDCl₃) 7.46 (1H, d), 7.12 (1H, d), 7.09 (1H, bs), 4.36 (1H, m), 3.34 (2H, m), 2.83 (3H, s), 1.94 (2H, m), 1.71 (2H, m), 1.33 (13H, m), 0.90 (3H, t).

b) 3-[2-Chloro-5-(trifluoromethyl)phenoxy]-N-methyl-1-heptanamine hydrochloride

The title compound was prepared according to the method of Example 1 step (d) but using [[3-[2-chloro-5-(trifluoromethyl)phenoxy]heptyl]methylcarbamic acid, 1,1-dimethylethyl ester.

MS APCI+ve $^m/z$ 324 ([M+H]⁺). ¹H NMR 300 MHz (d₆-DMSO) 7.67 (1H, d), 7.55 (1H, d), 7.31 (1H, dd), 6.43 (2H, s), 4.78 (1H, m), 2.87 (2H, m), 2.47 (3H, s), 1.95 (2H, m), 1.63 (2H, m), 1.24–1.36 (4H, m), 0.90 (3H, t).

EXAMPLE 16

3-[(2,5-Dichlorophenyl)thio]-N-methyl-1-hexanamine hydrochloride

To a stirred solution of triphenylphosphine (1.13 g, 4.32 mmol) in dry tetrahydrofuran (12 ml) at 0° C. was added diisopropyl azodicarboxylate (0.88 ml, 4.32 mmol) dropwise under nitrogen. After 0.5 h, a solution of (3-hydroxyhexyl)methylcarbamic acid 1,1-dimethylethyl ester (0.5 g, 2.16 mmol) and 2,5-dichlorobenzenethiol (0.27 ml, 2.16 mmol) in dry tetrahydrofuran (6 ml) was added slowly at 0° C. The reaction mixture was stirred at 0° C. for 1 h, then overnight at room temperature. The mixture was then evaporated, treated with ether, the precipitated solid filtered off and the filtrate evaporated The residue was eluted down a flash chromatography column using 10% ether/isohexane to give 492 mg of the intermediate carbamate as a colourless oil. This material was stirred 10 with 4M hydrogen chloride in dioxan (6 ml) for 1 h, concentrated and the residue triturated with ether and filtered to give 392 mg (55%) of the title compound as a colourless solid.

MS APCI+ve$^m$/z 292 ([M+H]$^+$). $^1$H NMR 300 MHz (d$_6$-DMSO) 8.77 (2H, brs), 7.57 (1H, d), 7.53 (1H, d), 7.31 (1H, d of d), 3.68 (1H, m), 3.02 (2H, t), 2.54 (3H, s), 1.94 (2H, m), 1.59 (2H, m), 1.44 (2H, m), 0.9 (3H, t).

EXAMPLE 17

4-Chloro-2-[1-ethyl-3-(methylamino)propoxy]-5-fluorobenzonitrile hydrochloride a) [3-(5-Chloro-2-cyano-4-fluorophenoxy)pentyl]methylcarbamic acid, 1,1-dimethylethyl ester The subtitle compound was prepared according to the method of Example 3 step (b) using (3-hydroxypentyl)methylcarbamic acid, 1,1-dimethylethyl ester and 4-chloro-2,5-difluorobenzonitrile in N,N-dimethylformamide.

$^1$H NMR 300 MHz (CDCl$_3$) 7.33 (1H, d), 6.99 (1H, s), 4.26 (1H, m), 3.34 (2H, m), 2.85 (3H, s), 1.96 (2H, m), 1.74 (2H, m), 1.41 (9H, s), 0.99 (3H, t).

b) 4-Chloro-2-[1-ethyl-3-(methylamino)propoxy]-5-fluorobenzonitrile hydrochloride The subtitle compound was prepared according to the method of Example 2 step (c) using [3-(5-chloro-2-cyano-4-fluorophenoxy)pentyl]methylcarbamic acid, 1,1-dimethylethyl ester.

MS APCI+ve$^m$/z 271/3([M+H]$^+$). $^1$H NMR 300 MHz (d$_6$-DMSO) 8.82 (2H, d), 8.02 (1H, d), 7.71 (1H, d), 4.74 (1H, m), 2.98 (2H, m), 2.55 (3H, s), 2.01 (2H, q), 1.66 (2H, m), 0.91 (3H, t).

EXAMPLE 18

4-Chloro-5-fluoro-2-[1-[2-(methylamino)ethyl]butoxy]benzonitrile hydrochloride a) [3-(5-Chloro-2-cyano-4-fluorophenoxy)hexyl]methylcarbamic Acid, 1,1-dimethylethyl ester The subtitle compound was prepared according to the method of Example 3 step (b) using (3-hydroxyhexyl)methylcarbamic acid, 1,1-dimethylethyl ester and 4-chloro-2,5-difluorobenzonitrile in N,N-dimethylformamide.

$^1$H NMR 300 MHz (CDCl$_3$) 7.33 (1H, d), 6.99 (1H, bs), 4.33 (1H, m), 3.34 (2H, m), 2.85 (3H, s), 1.95 (2H, m), 1.70 (2H, m), 1.41 (11H, m), 0.95 (3H, t).

b) 4-Chloro-5-fluoro-2-[1-[2-(methylamino)ethyl]butoxy]benzonitrile hydrochloride The subtitle compound was prepared according to the method of Example 2 step (c) using [3-(5-chloro-2-cyano-4-fluorophenoxy)hexyl]methylcarbamic acid, 1,1-dimethylethyl ester.

MS APCI+ve$^m$/z 285/7([M+H]$^+$). $^1$H NMR 300 MHz (d$_6$-DMSO) 8.74 (2H, bs), 8.02 (1H, d), 7.71 (1H, d), 4.78 (1H, m), 3.01 (2H, m), 2.55 (3H, s), 2.01 (2H, m), 1.63 (2H, m), 1.38 (2H, m), 0.90 b(3H, t).

EXAMPLE 19

3-(5-Chloro-2-nitrophenoxy)-N-methyl-1-hexanamine oxalate a) [3-(5-Chloro-2-nitrophenoxy)hexyl]methylcarbamic acid 1,1-dimethylethyl ester The subtitle compound was prepared according to the method of Example 3 step (b) using (3-hydroxyhexyl)methylcarbamic acid, 1,1-dimethylethyl ester and 4-chloro-2-fluoronitrobenzene in N,N-dimethylformamide.

MS APCI+ve$^m$/z 287/9 ([M+H-Boc]$^+$). $^1$H NMR 300 MHz (CDCl$_3$) 7.77 (1H, d), 6.96 (2H, m), 4.42 (1H, m), 3.36 (2H, t), 2.84 (3H, s), 1.95 (2H, m), 1.70 (2H, m), 1.41 (11H, m), 0.94 (3H, t).

b) 3-(5-Chloro-2-nitrophenoxy)-N-methyl-1-hexanamine oxalate

[3-(5-chloro-2-nitrophenoxy)hexyl]methylcarbamic acid, 1,1-dimethylethyl ester (130 mg, 0.336 mmol) was dissolved in 4M hydrogen chloride in dioxane (10 ml). The resulting solution was stirred at room temperature for 3 h, then diluted with sodium bicarbonate solution containing ammonia and extracted three times with dichloromethane. The combined organic fractions were washed with brine then dried over magnesium sulphate. The solvent was evaporated and the residue dissolved in ethanol. To this solution was added oxalic acid in ethanol and the solvent evaporated. The residue was recrystallised from ethanol to give 90 mg (71%) of the title compound as a white solid.

MS APCI+ve$^m$/z 287/9([M+H]$^+$). $^1$H NMR 300 MHz (d$_6$-DMSO) 7.93 (1H, d), 7.58 (1H, d), 7.20 (1H, dd), 4.84 (1H, m), 2.96 (2H, m), 2.55 (3H, s), 1.96 (2H, m), 1.61 (2H, m), 1.34 (2H, m), 0.88 (3H, t).

EXAMPLE 20

4-Chloro-2-[3-(methylamino)-1-(trifluoromethyl)propoxy]benzonitrile a) Methyl-(4,4,4-trifluoro-3-hydroxybutyl)carbamic acid, 1,1-dimethylethyl ester Methyl-(3-oxopropyl)carbamic acid, 1,1-dimethylethyl ester (320 mg, 1.71 mmol) and (trifluoromethyl)trimethylsilane (298 mg, 2.10 mmol) were dissolved in tetrahydrofuran (10 ml) under nitrogen and cooled to 0° C. with stirring. To the resulting solution was added tetrabutylammonium fluoride (1.0M solution in tetrahydrofuran, 1.0 ml, 1.0 mmol) and the mixture was then allowed to warm to room temperature with stirring over 20 h. The mixture was then poured into saturated ammonium chloride solution and then extracted with diethyl ether three times. The combined organic fractions were then washed with brine and dried over magnesium sulphate. The solvent was evaporated and the residue eluted down a flash chromatography column using 50% diethyl ether/isohexane as eluent to give 290 mg (66%) of the title compound as an oil.

$^1$H NMR 300 MHz (CDCl$_3$) 4.95 (1H, bs), 3.86 (2H, m), 3.01 (1H, m), 2.87 (3H, s), 1.86 (1H, m), 1.70 (1H, m), 1.47 (9H, s).

b) [3-(5-Chloro-2-cyanophenoxy)-4,4,4-trifluorobutyl]methylcarbamic acid, 1,1-dimethylethyl ester The subtitle compound was prepared according to the method of Example 3 step (b) using methyl-(4,4,4-trifluoro-3-hydroxybutyl)carbamic acid, 1,1-dimethyl ethyl ester and 4-chloro-2-fluorobenzonitrile in N,N-dimethylformamide.

$^1$H NMR 300 MHz (CDCl$_3$) 7.52 (1H, d), 7.10 (2H, m), 4.69 (1H, m), 3.70 (1H, bm), 3.29 (1H, bm), 2.85 (3H, s), 2.17 (2H, m), 1.38 (9H, s).

c) 4-Chloro-2-[3-(methylamino)-1-(trifluoromethyl) propoxy]benzonitrile hydrochloride The title compound was prepared according to the method of Example 2 step (c) using [3-(5-chloro-2-cyanophenoxy)-4,4,4-trifluorobutyl]methylcarbamic acid, 1,1-dimethylethyl ester.

MS APCI+ve$^m$/z 293/5([M+H]$^+$). $^1$H NMR 300 MHz (d$_6$-DMSO) 8.86 (2H, br s), 7.89 (1H, d), 7.81 (1H, d), 7.36 (1H, dd), 5.75 (1H, m), 3.09 (2H, m), 2.59 (3H, s), 2.21–2.33 (2H, m).

EXAMPLE 21

4-Chloro-5-fluoro-2-[3-(methylamino)-1-(trifluoromethyl)propoxy]benzonitrile hydrochloride a) [3-(5-Chloro-2-cyano-4-fluorophenoxy)-4,4,4-trifluorobutyl]methylcarbamic acid, 1,1-dimethylethyl ester The subtitle compound was prepared according to the method of Example 3 step (b) using methyl-(4,4,4-trifluoro-3-hydroxybutyl)carbamic acid, 1,1-dimethylethyl ester and 4-chloro-2,5-difluorobenzonitrile in N,N-dimethylformamide.

$^1$H NMR 300 MHz (CDCl$_3$) 7.37 (1H, d), 7.30 (1H, bm), 4.62 (1H, m), 3.80 (1H, bm), 3.20 (1H, bm), 2.86 (3H, s), 2.16 (2H, m), 1.40 (9H, s).

b) 4-Chloro-5-fluoro-2-[3-(methylamino)-1-(trifluoromethyl)propoxy]benzonitrile hydrochloride The title compound was prepared according to the method of Example 2 step (c) using [3-(5-chloro-2-cyano-4-fluorophenoxy)-4,4,4-trifluorobutyl]methylcarbamic acid, 1,1-dimethylethyl ester.

MS APCI+ve$^m$/z 311/3 ([M+H]$^+$). $^1$H NMR 300 MHz (d$_6$-DMSO) 8.89 (2H, bs), 8.14 (1H, d), 8.00 (1H, d), 5.70 (1H, m), 3.04–3.17 (2H, m), 2.59 (3H, s), 2.18–2.35 (2H, m).

EXAMPLE 22

4-Chloro-5-fluoro-[[1-[2-(methylamino)ethyl]-2-propenyl]oxy]benzonitrile hydrochloride a) (3-Hydroxy-4-pentenyl)methylcarbamic Acid 1,1-dimethylethyl ester The subtitle compound was prepared according to the method of Example 1 step (b) using vinylmagnesium bromide.

$^1$H NMR 300 MHz (CDCl$_3$) 5.90 (1H, m), 5.27 (1H, d), 5.10 (1H, d), 4.02 (2H, m), 3.80 (1H, m), 3.02 (1H, m), 2.85 (3H, s), 1.75 (1H, m), 1.45 (9H, s).

b) [3-(5-Chloro-2-cyano-4-fluorophenoxy)-4-pentenyl] methylcarbamic Acid, 1,1-dimethylethyl ester The subtitle compound was prepared according to the method of Example 3 step (b) using (3-hydroxy-4-pentenyl) methylcarbamic acid, 1,1-dimethylethyl ester and 4-chloro-2,5-difluorobenzonitrile in N,N-dimethylformamide.

$^1$H NMR 300 MHz (CDCl$_3$) 7.33 (1H, d), 7.00 (1H, d), 5.85 (1H, m), 5.30 (2H, m), 4.65 (1H, m), 3.35–3.51 (2H, m), 2.87 (3H, s), 1.97–2.10 (2H, m), 1.41 (9H, s).

c) 4-Chloro-5-fluoro-[[1-[2-(methylamino)ethyl]-2-propenyl]oxy]benzonitrile hydrochloride The title compound was prepared according to the method of Example 2 step (c) using [3-(5-chloro-2-cyano-4-fluorophenoxy)-4-pentenyl]methylcarbamic acid, 1,1-dimethylethyl ester.

MS APCI+ve$^m$/z 269/271 ([M+H]$^+$). $^1$H NMR 300 MHz (d$_6$-DMSO) 8.81 (2H, bs), 8.05 (1H, d), 7.55 (1H, d), 5.87 (1H, m), 5.36 (1H, dd), 5.24 (1H, q), 3.00 (2H, m), 2.57 (3H, s), 2.10 (2H, m).

EXAMPLE 23

4-Chloro-2-[1-cyclopentyl-3-(methylamino) propoxy]-5-fluorobenzonitrile hydrochloride a) (3-Cyclopentyl-3-hydroxypropyl)methylcarbamic Acid, 1,1-dimethylethyl ester The subtitle compound was prepared according to the method of Example 1 step (b) using cyclopentylmagnesium chloride (2.0M in diethyl ether).

$^1$H NMR 300 MHz (CDCl$_3$) 2.84–3.90 (5H, bm), 2.86 (3H, s), 1.14–1.94 (9H, m), 1.47 (9H, s).

b) [3-(5-Chloro-2-cyano-4-fluorophenoxy)-3-cyclopentylpropyl]methylcarbamic Acid, 1,1-dimethylethyl ester The subtitle compound was prepared according to the method of Example 3 step (b) using (3-cyclopentyl-3-hydroxypropyl)methylcarbamic acid, 1,1-dimethylethyl ester and 4-chloro-2,5-difluorobenzonitrile in N,N-dimethylformamide.

$^1$H NMR 300 MHz (CDCl$_3$) 7.32 (1H, d), 7.04 (1H, bm), 4.28 (1H, m), 3.35 (2H, bm), 2.83 (3H, s), 2.28 (1H, m), 1.95 (2H, q), 1.50–1.80 (6H, m), 1.42 (9H, s), 1.26–1.45 (2H, m).

c) 4-Chloro-2-[1-cyclopentyl-3-(methylamino)propoxy]-5-fluorobenzonitrile hydrochloride The title compound was prepared according to the method of Example 2 step (c) using [3-(5-chloro-2-cyano-4-fluorophenoxy)-3-cyclopentylpropyl]methylcarbamic acid, 1,1-dimethylethyl ester.

MS APCI+ve$^m$/Z 311 ([M+H]$^+$). $^1$H NMR 300 MHz (d$_6$-DMSO) 8.66 (2H, bs), 8.02 (1H, d), 7.75 (1H, d), 4.71 (1H, m), 3.00 (2H, m), 2.54 (3H, s), 2.18 (1H, m), 2.00 (2H, m), 1.45–1.80 (6H, m).

EXAMPLE 24

4-Chloro-2-{[1-[2-(methylamino)ethyl]butyl]thio) benzonitrile hydrochloride a) [3-(Benzoylthio)hexyl]methylcarbamic Acid 1,1-dimethylethyl ester To a stirred solution of triphenylphosphine (1.13 g, 4.32 mmol) in dry tetrahydrofuran (12 ml) was added diisopropyl azodicarboxylate (0.88 ml, 4.32 mmol) dropwise with stirring at 0° C. under nitrogen. After stirring for 0.5 h, a solution of (3-hydroxyhexyl)methylcarbamic acid, 1,1-dimethylethyl ester (500 mg, 2.16 mmol) and thiobenzoic acid (0.51 ml, 4.3 mmol) in dry tetrahydrofuran (10 ml) was added at 0° C. The reaction mixture was stirred at 0° C. for 1 h, and then stirred at room temperature overnight. The mixture was evaporated, the residue dissolved in toluene and eluted down a flash chromatography column using 10% ether/isohexane as eluent to give 420 mg (55%) of product as a pale yellow oil.

$^1$H NMR 400 MHz (CDCl$_3$) 7.97 (2H, d), 7.56 (1H, m), 7.44 (2H, m), 3.75 (1H, t), 3.30 (2H, m), 2.85 (3H, s), 2.85 (2H, m), 1.65 (2H, m), 1.45 (9H, s), 1.44(2H, m), 0.93 (3H, t).

b) 4-Chloro-2-{[1-[2-(methylamino)ethyl]butyl] thio}benzonitrile hydrochloride 2-methoxyethanamine (352 μl, 4.06 mmol) before being heated to 60° C. for 5 days. The mixture was filtered and purified via RP-HPLC on the crude reaction material. The purified compound was then treated with 50% saturated oxalic acid in ether to produce a white powder which was collected via filtration. (378 mg, 15%).

MS APCI+ve$^m$/z 315 ([M+H]$^+$). $^1$H NMR 300 MHz (d$_6$-DMSO) 8.03 (1H, d), 7.65 (1H, d), 4.66 (1H, m), 3.56 (2H, m), 3.30 (3H, s), 3.14–3.06 (2H, m), 3.06–2.97 (2H, m), 2.03 (2H, m), 1.65 (2H, m), 0.92 (3H, t).

EXAMPLE 26

4-Bromo-2-{1-ethyl-3-[(2-methoxyethyl)amino] propoxy}benzonitrile oxalate

Prepared as in Example 25 but using 4-bromo-2-fluorobenzonitrile (1.63 g, 8.15 mmol) to give 190 mg (7%) of the title compound.

MS APCI+ve$^m$/z 342 ([M+H]$^+$). $^1$H NMR 300 MHz (d$_6$-DMSO) 7.71 (1H, d), 7.59 (1H, s), 7.34 (1H, s), 4.74 (1H, m), 3.56 (2H, m), 3.30 (3H, s), 3.15–3.12 (2H, m), 3.12–2.97 (2H, m), 2.02 (2H, m), 1.66 (2H, m), 0.91 (3H, t).

EXAMPLE 27

4-Bromo-2-[3-(dimethylamino)-1-ethylpropoxy] benzonitrile oxalate

Prepared as in Example 26 but using no amine except for the dimethylamine produced via the degradation of N,N-dimethylformamide at 60° C.

MS APCI+ve$^m$/z 312 ([M+H]$^+$).

[3-(Benzoylthio)hexyl]methylcarbamic acid 1,1-dimethylethyl ester (400 mg, 1.14 mmol) in ethanol (20 ml) was treated with sodium hydroxide (100 mg, 2.5 mmol) in water (6 ml) followed by 4-chloro-2-fluorobenzonitrile (180 mg, 1.14 mmol) and the reaction mixture stirred at room temperature overnight under nitrogen. The mixture was diluted with water, and extracted three times with ethyl acetate. The extracts were combined, washed with brine and dried over anhydrous magnesium sulphate. The solvent was evaporated and the residue eluted down a flash chromatography column using 10% ether/isohexane as eluent to give the protected amine as an oil. This material was stirred with 4M hydrogen chloride in dioxan (6 ml) for 1.5 h, evaporated and the residue triturated three times with dry ether to give 172 mg (47%) of the required product as the hydrochloride salt.

MS APCI+ve$^m$/z 283 ([M+H]$^+$). $^1$H NMR 300 MHz (d$_6$-DMSO) 8.80 (2H, br s), 7.90 (1H, d), 7.81 (1H, d), 7.52 (1H, d of d), 3.79 (1H, m), 3.03 (2H, t), 2.54 (3H, s), 1.96 (2H, m), 1.61 (2H, m), 1.48 (2H, m), 0.89 (3H, t).

EXAMPLE 25

4-Chloro-2-[1-ethyl-3-[(2-methoxyethyl)amino] propoxy]-5-fluorobenzonitrile oxalate 1-Chloro-3-pentanol (1 g, 8.15 mmol) was dissolved in tetrahydrofuran (20 ml) and treated with sodium hydride as a 60% suspension in mineral oil (480 mg, 12.2 mmol) followed after 10 minutes by 4-chloro-2,5-difluorobenzonitrile (1.41 g, 8.15 mmol). The mixture was stirred at room temperature for 18 h before being treated with methanol (1 ml) and then water (10 ml). The tetrahydrofuran was then removed via heating the vessel to 80° C. and applying a nitrogen stream. Once the tetrahydrofuran was evaporated off, the residue was extracted into dichloromethane, dried over magnesium sulphate and concentrated in vacuo. The resultant material was re-dissolved into N,N-dimethylformamide (8 ml) and treated with sodium iodide (305 mg, 2.03 mmol), triethylamine (565 µl, 4.06 mmol) and $^1$H NMR 300 MHz (d$_6$-DMSO) 7.70 (1H, d), 7.60 (1H, s), 7.32 (1H, d), 4.71 (1H, m), 3.09 (2H, m), 2.73 (6H, s), 2.04 (2H, m), 1.67 (2H, m), 0.91 (3H, t).

EXAMPLE 28

4-Chloro-2-[3-(dimethylamino)-1-ethylpropoxy]-5-fluorobenzonitrile oxalate

Prepared as in Example 25 but using no amine except for the dimethylamine produced via the degradation of N,N-dimethylformamide at 60° C.

MS APCI+ve$^m$/z 285([M+H]$^+$). $^1$H NMR 300 MHz (d$_6$-DMSO) 8.04 (1H, d), 7.67 (1H, d), 4.67 (1H, m), 3.01 (2H, m), 2.77 (6H, s), 2.03 (2H, m), 1.66 (2H, m), 0.91 (3H, t).

EXAMPLE 29

2-[[(1R)-3-Amino-1-(methoxymethyl)propyl]oxy]-4-chloro-benzonitrile oxalate a) Methyl (2S)-4-amino-2-hydroxy-butanoate hydrochloride (S)-(–)-4-Amino-2-hydroxybutyric acid (5.432 g, 45.6 mmol) was dissolved in methanol (250 ml) and chlorotrimethylsilane (4.86 g, 137 mmol) added. The reaction was gently refluxed for 20 h. The reaction was cooled and the solvent removed in vacuo to afford the title compound as a colourless oil (6.07 g, 100%).

$^1$H NMR 300 MHz (d$_6$-DMSO) 8.05 (3H, bs), 4.59 (1H, bs), 4.23–4.18 (1H, m), 3.66 (3H, s), 2.92–2.80 (2H, m), 2.04–1.92 (1H, m), 1.88–1.76 (1H, m).

b) Methyl (2S)-4-[[(1,1-dimethylethoxy)carbonyl] amino]-2-hydroxy-butanoate

The product of step (a) (6.07 g, 45.6 mmol) was dissolved in anhydrous dimethylformamide and triethylamine (25.1 ml, 0.18 mol) added. Di-tert-butyl dicarbonate (9.954 g, 45.6 mmol) was added immediately, in one portion, and the reaction stirred at room temperature for 20 h. Water (75 ml) was added and the reaction extracted with ethyl acetate (3×80 ml). The combined organic extracts were washed with water (6×30 ml), dried (magnesium sulphate) and evaporated in vacuo to give the title compound as a colourless oil (6.719 g, 63%).

$^1$H NMR 300 MHz (CDCl$_3$) 4.82 (1H, bs), 4.29–4.23 (1H, m), 3.79 (3H, s), 3.38 (1H, bs), 3.33–3.25 (2H, m), 2.05–1.98 (1H, m), 1.89–1.79 (1H, m), 1.44 (9H, s).

c) Methyl (2R)-2-(5-chloro-2-cyanophenoxy)-4-[[)1,1-dimethylethoxy)-carbonyl]amino]butanoate The product of step (b) (3.25 g, 13.9 mmol), 4-chloro-2-hydroxybenzonitrile (2.14 g, 13.9 mmol) and triphenylphosphine (4.38 g, 16.7 mmol) were dissolved in anhydrous tetrahydrofuran (80 ml) and the solution cooled to 0° C. Diethyl azodicarboxylate (2.91 g, 16.7 mmol) was added dropwise and the solution allowed to warm to room temperature, then stirred for 2 days. The solvent was removed in vacuo and the residue chromatographed on flash silica, eluting with hexane:ethyl acetate (3:1), to afford the title compound as a white solid (3.562 g, 69%).

$^1$H NMR 300 MHz (CDCl$_3$) 7.51 (1H, d), 7.06 (1H, dd), 6.81 (1H, s), 4.81 (1H, t), 4.79 (1H, bs), 3.79 (3H, s), 3.43–3.38 (2H, m), 2.30–2.23 (2H, m), 1.42 (9H, s).

d) 1,1-Dimethylethyl [(3R)-3-(5-chloro-2-cyanophenoxy)-4-hydroxybutyl]carbamate

The product from step (c) (881 mg, 2.39 mmol) was dissolved in anhydrous tetrahydrofuran (20 ml) and lithium borohydride (2M solution in tetrahydrofuran, 2.6 ml, 5.26 mmol) added dropwise. The mixture was stirred at room temperature for 18 h. Methanol (5 ml) was added and the reaction stirred for 15 minutes. The solvent was removed in vacuo and the residue chromatographed on flash silica, eluting with hexane:ethyl acetate (3:2, then 1:1) to give the title compound as a colourless oil (605 mg, 74%).

$^1$H NMR 400 MHz (CDCl$_3$) 7.48 (1H, d), 7.14 (1H, d), 7.02 (1H, dd), 4.72 (1H, bs), 4.57–4.51 (1H, m), 3.91–3.80 (2H, m), 3.32–3.27 (2H, m), 2.20 (1H, bs), 2.03–1.93 (2H, m), 1.43 (9H, s).

e) 1,1-Dimethylethyl [(3R)-3-(5-chloro-2-cyanophenoxy)-4-methoxybutyl]carbamate

The product from step (d) (380 mg, 1.12 mmol) was dissolved in acetonitrile (40 ml) and silver oxide (1.292 g, 5.58 mmol) and iodomethane (1.589 g, 11.2 mmol) added. The reaction was stirred at room temperature for 20 h, then at 60° C. for 3 days. The reaction was cooled and filtered. The filtrate was evaporated in vacuo and the residue chromatographed on flash silica, eluting with hexane:ethyl acetate (3:1, then 2:1), to afford the title compound as a colourless oil (146 mg, 37%).

$^1$H NMR 300 MHz (CDCl$_3$) 7.46 (1H, d), 7.15 (1H, d), 7.00 (1H, dd), 4.68 (1H, bs), 4.57–4.54 (1H, m), 3.60–3.57 (2H, m), 3.37 (3H, s), 3.32–3.28 (2H, m), 1.96–1.94 (2H, m), 1.42 (9H, s).

f) 2-[[(1R)-3-Amino-1-(methoxymethyl)propyl]oxy]-4-chlorobenzonitrile oxalate

The product from step (e) (140 mg, 0.39 mmol) was dissolved in 4M hydrochloric acid in dioxan and stirred at room temperature for 2 h. The solvent was removed in vacuo and the residue partitioned between ethyl acetate and aqueous saturated sodium bicarbonate solution. The organic layer was separated and washed with water (2×20 ml), dried (magnesium sulphate) and evaporated in vacuo. The residue was dissolved in ethyl acetate (5 ml) and treated with one equivalent of oxalic acid. The precipitated solid was filtered off and dried to give the title compound (30 mg, 22%).

MS APCI+ve $^m$/z 255 ([M+H]$^+$). $^1$H NMR 400 MHz (d$_6$-DMSO) 7.78 (1H, d), 7.52 (1H, s), 7.20 (1H, dd), 4.94–4.89 (1H, m), 3.59–3.52 (2H, m), 3.28 (3H, s), 2.96–2.88 (2H, m), 2.02–1.96 (2H, m).

Screens

The pharmacological activity of compounds according to the invention was tested in the following screens.

Screen 1

The activity of compounds of formula (I), or a pharmaceutically acceptable salt, enantiomer or racemate thereof, may be screened for nitric oxide synthase inhibiting activity by a procedure based on that of Förstermann et al., Eur. J. Pharm., 1992, 225, 161–165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% CO$_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 μl of substrate cocktail (50 mM Tris-HCl (pH 7.5 at 20° C.), 400 μM NADPH, 20 μM flavin adenine dinucleotide, 20 μM flavin mononucleotide, 4 μM tetrahydrobiopterin, 12 μM L-arginine and 0.025 mCi L-[$^3$H] arginine) is added to wells of a 96 well filter plate (0.45 μM pore size) containing 25 μl of a solution of test compound in 50 mM Tris-HCl. The reaction is started by adding 50 μl of cell lysate (prepared as above) and after incubation for 1 hour at room temperature is terminated by addition of 50 μl of an aqueous solution of 3 mM nitroarginine and 21 mM EDTA.

Labelled L-citrulline is separated from labelled L-arginine using Dowex AG-SOW. 150 μl of a 25% aqueous slurry of Dowex 50W (Na$^+$ form) is added to the assay after which the whole is filtered into 96 well plates. 75 μl of filtrate is sampled and added to wells of 96 well plates containing solid scintillant. After allowing the samples to dry the L-citrulline is quantified by scintillation counting.

In a typical experiment basal activity is 300 dpm per 75 μl sample which is increased to 1900 dpm in the reagent controls. Compound activity is expressed as IC$_{50}$ (the concentration of drug substance which gives 50% enzyme inhibition in the assay) and aminoguanidine, which gives an IC$_{50}$ (50% inhibitory concentration) of 10 μM, is tested as a standard to verify the procedure. Compounds are tested at a range of concentrations and from the inhibitions obtained IC$_{50}$ values are calculated. Compounds that inhibit the enzyme by at least 25% at 100 μM are classed as being active and are subjected to at least one retest.

Screen 2

Compounds also show activity against the human form of induced nitric oxide synthase as can be demonstrated in the following assay.

The human colorectal carcinoma cell line, DLD-1 (obtained from the European Collection of Animal Cell Culture—cell line number 90102540) was routinely grown in RPMI 1640 supplemented with 10% (v/v) foetal bovine serum, and 2 mM L-glutamine, at 37° C. in 5% CO$_2$.

Nitric oxide synthase was induced in cells by addition of medium containing human recombinant gamma-IFN (1000 units/ml), TNF-alpha (200 U/ml), IL-6 (200 U/ml) and IL-1-beta (250 U/ml). After incubation for 18 hours at 37° C., the medium was removed and the cells washed with warm phosphate buffered saline. Cells were incubated for a further 5 hours at 37° C./5% CO$_2$ in RPMI 1640 containing 100 μM L-arginine and 100 μM verapamil-HCl in the presence and absence of test compounds.

Nitrite accumulation was determined by mixing an equal volume of culture media with Griess reagent (10 mg/ml sulphanilamide, 1 mg N-(1-naphthyl)ethylenediamine in 1 ml 2.5% (v/v) phosphoric acid). Inhibition in the presence of compounds was calculated relative to the nitrite levels produced by untreated cells. $IC_{50}$ values were estimated from a semi-log plot of % inhibition versus concentration of compound.

When tested, the compounds of Examples 1 to 29 gave $IC_{50}$ values of less than 50 μM in at least one of the above screens, indicating that they are predicted to show useful therapeutic activity.

What is claimed is:

1. A compound of formula (I)

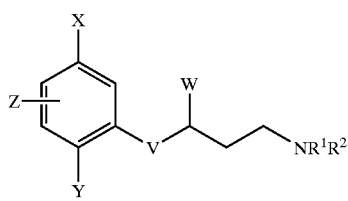

(I)

wherein:

X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;

m and p independently represent an integer 0, 1 or 2;

Z represents H or fluoro;

V represents O, $S(O)_n$ or $NR^3$;

W represents C1 to 4 alkyl, C2 to 4 alkenyl, C2 to 4 alkynyl, C3 to 6 cycloalkyl, pyrrolidine, piperidine, tetrahydrofuran or perhydroazepine; any of said groups being optionally further substituted by C1 to 4 alkyl, C1 to 4 alkoxy, C1 to 4 alkylthio, C3 to 6 cycloalkyl, halogen or phenyl; said phenyl group being optionally further substituted by one or more substituents selected independently from halogen, C1 to 4 alkyl, C1 to 4 alkoxy, $CF_3$, $OCF_3$, CN or $NO_2$;

$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl, furan, thiophene, pyridine, thiazole, imidazole, oxazole, triazole, ozadiazole, thiadiazole, pyrimidine, pyrrolidine, tetrahydrofuran, piperidine, and piperazine; said phenyl or aromatic heterocyclic ring being optionally further substituted by halogen, C1 to 4 alkyl, C1 to 4 alkoxy, $CF_3$, $OCF_3$, CN or $NO_2$;

or the group $NR^1R^2$ together represents a pyrrolidine, piperidine, piperazine, morpholine and perhydroazepine; said ring being optionally substituted by C1 to 4 alkyl, C1 to 4 alkoxy or OH; said alkyl group being optionally substituted by C1 to 4 alkoxy, OH or $NR^7R^8$;

$R^3$ represents H or C1 to 4 alkyl;

$R^4$ and $R^5$ independently represent H or C1 to 4 alkyl;

$R^6$ represents H or C1 to 6 alkyl; said alkyl group being optionally substituted by C1 to 4 alkoxy, OH, $NR^9R^{10}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

$R^7$, $R^8$, $R^9$ and $R^{10}$ independently represent H or C1 to 4 alkyl;

n represents an integer 0, 1 or 2;

or a pharmaceutically acceptable salt, enantiomer or racemate thereof;

with the proviso that when V represents O; and $R^1$ and $R^2$ each independently represent H or methyl; and W represents C5 to 6 cycloalkyl; then at least one of X and Y does not represent halogen, C1 to 4 alkyl, C1 to 3 alkoxy or $CF_3$.

2. A compound of formula (I), according to claim 1, wherein V represents O or S.

3. A compound of formula (I), according to claim 1, wherein the substituents X and Y are selected from Br, Cl, CN, $CF_3$ and $CH_3$.

4. A compound of formula (I), according to claim 1, wherein the substituents $R^1$ and $R^2$ are H and $CH_3$ respectively.

5. A compound of formula (I), according to claim 1, which is:

3-(2,5-dichlorophenoxy)-N-methyl-1-heptanamine;

3-(2,5-dichlorophenoxy)-N-methyl-1-pentanamine;

[3-cyclopropyl-3-(2,5-dichlorophenoxy)propyl]-N-methyl-1-propanamine;

3-(2,5-dichlorophenoxy)-N,5-dimethyl-1-hexanamine;

3-(2,5-dichlorophenoxy)-N-methyl-1-hexanamine;

4-chloro-2-[3-methyl-1-[2-(methylamino)ethyl]butoxy]benzonitrile;

4-chloro-2-[1-ethyl-3-(methylamino)propoxy]benzonitrile;

4-chloro-2-[1-[2-(methylamino)ethyl]butoxy]benzonitrile, 4-chloro-2-[1-[2-(methylamino)ethyl]pentyloxy]benzonitrile;

4-chloro-2-[1-cyclopropyl-3-(methylamino)propoxy]benzonitrile;

4-chloro-2-[3-(methylamino)-1-(phenylmethyl)propoxy]benzonitrile;

3-(5-chloro-2-nitrophenoxy)-N-methyl-1-heptanamine;

3-(5-chloro-2-nitrophenoxy)-N-methyl-1-pentanamine;

3-[2-chloro-5-(trifluoromethyl)phenoxy]-N-methyl-1-pentanamine;

3-[2-chloro-5-(trifluoromethyl)phenoxy]-N-methyl-1-heptanamine;

3-[(2,5-dichlorophenyl)thio]-N-methyl-1-hexanamine;

4-chloro-2-[1-ethyl-3-(methylamino)propoxy]-5-fluorobenzonitrile;

4-chloro-5-fluoro-2-[1-[2-(methylamino)ethyl]butoxy]benzonitrile;

3-(5chloro-2-nitrophenoxy)-N-methyl-1-hexanamine;

4-chloro-2-[3-(methylamino)-1-(trifluoromethyl)propoxy]benzonitrile;

4-chloro-5-fluoro-2-[3-(methylamino)-1-(trifluoromethyl)propoxy]benzonitrile;

4-chloro-5-fluoro-[[1-[2-(methylamino)ethyl]-2-propenyl]oxy]benzonitrile;

4-chloro-2-[1-cyclopentyl-3-(methylamino)propoxy]-5-fluorobenzonitrile;

4-chloro-2-{[1-[2-(methylamino)ethyl]butyl]thio)benzonitrile;

4-chloro-2-[1-ethyl-3-[(2-methoxyethyl)amino]propoxy]-5-fluorobenzonitrile;

4-bromo-2-{1-ethyl-3-[(2-methoxyethyl)amino]
propoxy}benzonitrile;
4-bromo-2-[3-(dimethylamino)-1-ethylpropoxy]
benzonitrile;
4-chloro-2-[3-(dimethylamino)-1-ethylpropoxy]-5-
fluorobenzonitrile;
2-[[(1R)-3-amino-1-(methoxymethyl)propyl]oxy]-4-
chloro-benzonitrile;
or a pharmaceutically acceptable salt, enantiomer or racemate thereof.

6. A pharmaceutical composition comprising a compound of formula (I) according to claim 1, or a pharmaceutically acceptable salt, enantiomer or racemate thereof, in admixture with a pharmaceutically acceptable adjuvant, diluent or carrier.

7. A method of treating, or reducing the risk of, inflammatory disease in a person suffering from, or at risk of, said disease, wherein the method comprises administering to the person a therapeutically effective amount of a compound of formula (I), as defined in claim 1, or a pharmaceutically acceptable salt, enantiomer or racemate thereof.

8. The method of treatment as claimed in claim 7 wherein the disease is inflammatory bowel disease.

9. The method of treatment as claimed in claim 7 wherein the disease is rheumatoid arthritis.

10. The method of treatment as claimed in claim 7 wherein the disease is osteoarthritis.

11. A method of treating, or reducing the risk of, pain in a person suffering from, or at risk of, said condition, wherein the method comprises administering to the person a therapeutically effective amount of a compound of formula (I), as defined in claim 1, or a pharmaceutically acceptable salt, enantiomer or racemate thereof.

12. A method of treating, or reducing the risk of, inflammatory
disease in a person suffering from, or at risk of, said disease, wherein the method comprises administering to the person a therapeutically effective amount of a combination of a compound of formula (I), as defined in claim 1, or a pharmaceutically acceptable salt, enantiomer or racemate thereof, with a COX-2 inhibitor.

13. A process for the preparation of a compound of formula (I), as defined in claim 1, or a pharmaceutically acceptable salt, enantiomer or racemate thereof, wherein the process comprises:

(a) reaction of a compound of formula (II)

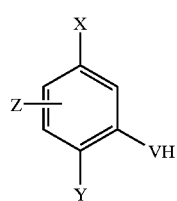

(II)

wherein X, Y, Z and V are as defined in claim 1, with a compound of formula (III)

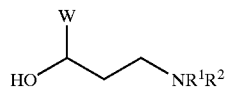

(III)

wherein W, $R^1$ and $R^2$ are as defined in claim 1; or (b) reaction of a compound of formula (IV)

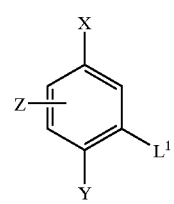

(IV)

wherein X, Y and Z are as defined in claim 1 and $L^1$ represents a leaving group, with a compound of formula (V)

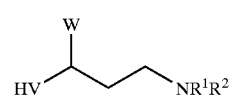

(V)

wherein $R^1$, $R^2$, V and W are as defined in claim 1; or (c) reaction of a compound of formula (VI)

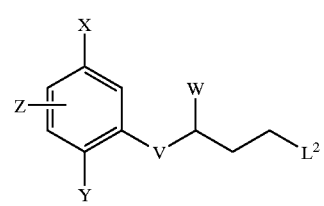

(VI)

wherein X, Y, V, W and Z are as defined in claim 1 and $L^2$ is a leaving group, with a compound of formula (VII)

(VII)

wherein $R^1$ and $R^2$ are as defined in claim 1; or (d) reaction of a compound of formula (II)

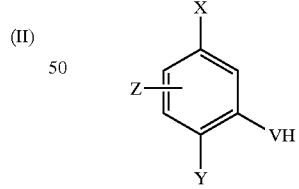

(II)

wherein X, Y, Z and V are as defined in claim 1, with a compound of formula (VIII)

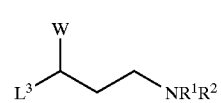

(VIII)

wherein $R^1$, $R^2$ and W are as defined in claim 1 and $L^3$ is a leaving group; or (e) reduction of a compound of formula (IX)

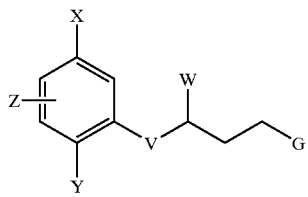

wherein X, Y, V, W and Z are as defined in claim 1 and G represents a group that upon reduction is converted into a group $NR^1R^2$.

14. The process of claim 13, further comprising converting the compound of formula (I) or a salt of formula (I) into a pharmaceutically acceptable salt thereof.

15. The process of claim 13, further comprising converting the compound of formula (I) into a further compound of formula (I).

16. The process of claim 13, further comprising converting the compound of formula (I) into an optical isomer thereof.

* * * * *

UNITED STATES PATENT AND TRADEMARK OFFICE
CERTIFICATE OF CORRECTION

PATENT NO. : 6,900,243 B2
DATED : May 31, 2005
INVENTOR(S) : David Cheshire et al.

It is certified that error appears in the above-identified patent and that said Letters Patent is hereby corrected as shown below:

Title page,
Item [73], Assignee, delete "Södertalge" and insert -- Södertälje --.

Column 28,
Line 54, delete "(5chloro" and insert -- (5-chloro --.

Signed and Sealed this

Seventeenth Day of January, 2006

JON W. DUDAS
*Director of the United States Patent and Trademark Office*